(12) United States Patent
Oshinski et al.

(10) Patent No.: US 12,706,205 B2
(45) Date of Patent: Aug. 11, 2026

(54) SYSTEM, METHOD, AND DEVICE FOR MEDICAL WASTE TRACKING

(71) Applicant: Becton, Dickinson and Company, Franklin Lakes, NJ (US)

(72) Inventors: Matthew Oshinski, Oak Ridge, NJ (US); Ashley Rachel Rothenberg, Morris Plains, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 29 days.

(21) Appl. No.: 18/028,889

(22) PCT Filed: Sep. 29, 2021

(86) PCT No.: PCT/US2021/052519
§ 371 (c)(1),
(2) Date: Mar. 28, 2023

(87) PCT Pub. No.: WO2022/072400
PCT Pub. Date: Apr. 7, 2022

(65) Prior Publication Data

US 2023/0343445 A1 Oct. 26, 2023

Related U.S. Application Data

(60) Provisional application No. 63/084,619, filed on Sep. 29, 2020.

(51) Int. Cl.
*G16H 40/20* (2018.01)
*A61M 25/00* (2006.01)
*G16H 40/40* (2018.01)

(52) U.S. Cl.
CPC .......... *G16H 40/20* (2018.01); *A61M 25/002* (2013.01); *G16H 40/40* (2018.01);
(Continued)

(58) Field of Classification Search
CPC ..... G16H 40/20; G16H 40/40; A61M 25/002; A61M 2205/3306; A61M 2205/3375;
(Continued)

(56) References Cited

U.S. PATENT DOCUMENTS 8,296,243 B2 10/2012 Mallett et al.
8,606,596 B1 12/2013 Bochenko et al.
(Continued)

FOREIGN PATENT DOCUMENTS

CN 109592256 A 4/2019
JP 2005082381 A 3/2005
(Continued)

OTHER PUBLICATIONS

Refonaa, J., & Vivek, J. (Mar. 2015). Tracking of bio medical waste using global positioning system. In 2015 International Conference on Circuits, Power and Computing Technologies [ICCPCT-2015] (pp. 1-5). IEEE. (Year: 2015).*
(Continued)

*Primary Examiner* — Winston R Furtado
(74) *Attorney, Agent, or Firm* — The Webb Law Firm

(57) ABSTRACT

A medical waste tracking device may include a housing including an opening configured to receive a medical device and a package for the medical device and/or a sensor configured to determine first identifying information from the package for the medical device and second identifying information from the medical device. One or more processors may be programmed and/or configured to determine, based on the first identifying information, that the medical device is in use; and determine, based on the second identifying information, that the medical device is not in use.

15 Claims, 9 Drawing Sheets

(52) U.S. Cl.
CPC ............... *A61M 2205/3306* (2013.01); *A61M 2205/3375* (2013.01); *A61M 2205/3393* (2013.01); *A61M 2205/3561* (2013.01); *A61M 2205/6009* (2013.01)

(58) Field of Classification Search
CPC .. A61M 2205/3393; A61M 2205/3561; A61M 2205/6009
USPC .............................................................. 705/2
See application file for complete search history.

(56) References Cited

U.S. PATENT DOCUMENTS

2006/0253297 A1* 11/2006 Mallett .................. G06Q 10/30 705/308
2007/0080223 A1 4/2007 Japuntich
2008/0195247 A1* 8/2008 Mallett ................... G07F 11/62 700/231
2012/0226446 A1* 9/2012 Nelson ................... G16H 40/60 73/61.41
2013/0325727 A1* 12/2013 MacDonell ............ A61B 50/10 705/308
2014/0008259 A1 1/2014 Maness
2014/0262553 A1* 9/2014 Pollock ................. B65F 1/1415 177/1
2015/0127362 A1 5/2015 DeBusk et al.
2018/0078326 A1 3/2018 Sall et al.
2019/0358387 A1* 11/2019 Elbadry ................. G01N 15/06
2020/0187870 A1* 6/2020 Bosque ................ A61B 5/1455
2020/0372318 A1* 11/2020 Bryant ..................... H04B 5/77
2022/0115106 A1 4/2022 Isaacson
2022/0118240 A1 4/2022 Brand et al.

FOREIGN PATENT DOCUMENTS

KR 1020130055675 A 5/2013
WO 2020163297 A1 8/2020
WO 2020163304 A1 8/2020

OTHER PUBLICATIONS

Macklin, D. (May 2010). Catheter management. In Seminars in oncology nursing (vol. 26, No. 2, pp. 113-120). WB Saunders. (Year: 2010).*

* cited by examiner

SYSTEM, METHOD, AND DEVICE FOR MEDICAL WASTE TRACKING

CROSS-REFERENCE TO RELATED APPLICATIONAPPLICATIONS

This application is the United States national phase of International Patent Application No. PCT/US2021/062519 filed September 29. 2021, and claims priority to U.S. Provisional Application Ser. No. 63/084,619, entitled "System, Method, and Device for Medical Waste Tracking", filed Sep. 29, 2020, the entire disclosures of which are hereby incorporated by reference in their entirety.

BACKGROUND

1. Field

The present disclosure relates generally to medical waste disposal and, in some non-limiting embodiments or aspects, to tracking medical waste disposal to determine medical device usage.

2. Technical Considerations

Medical facilities include waste receptacles, such as garbage bins, rubbish collections, waste baskets, recycling containers, sharps containers, and/or the like, for collecting medical waste. Existing systems for disposing of medical waste may determine an amount of the disposed waste or sort the medical waste according to applicable rules. However, these existing systems do not collect and/or provide information associated with medical device usage.

SUMMARY

Accordingly, provided are improved systems, devices, products, apparatus, and/or methods for medical waste tracking.

According to some non-limiting embodiments or aspects, provided is a method including: receiving, with an opening in a housing of a medical waste tracking device, a package for a medical device; determining, with a sensor of the medical waste tracking device, first identifying information from the package for the medical device; determining, with at least one processor, based on the first identifying information, that the medical device is in use; receiving, with the opening in the housing of the medical waste tracking device, the medical device; determining, with the sensor of the medical waste tracking device, second identifying information from the medical device; and determining, with at least one processor, based on the second identifying information, that the medical device is not in use.

According to some non-limiting embodiments or aspects, provided is a system including: a medical waste tracking device including: a housing including an opening configured to receive a medical device and a package for the medical device; and a sensor configured to determine first identifying information from the package for the medical device and second identifying information from the medical device; and one or more processors programmed and/or configured to: determine, based on the first identifying information, that the medical device is in use; and determine, based on the second identifying information, that the medical device is not in use.

According to some non-limiting embodiments or aspects, provided is a medical waste tracking device including: a housing including an opening configured to receive a medical device and a package for the medical device; and a sensor configured to determine first identifying information from the package for the medical device and second identifying information from the medical device; and one or more processors programmed and/or configured to: determine, based on the first identifying information, that the medical device is in use; and determine, based on the second identifying information, that the medical device is not in use.

Further non-limiting embodiments or aspects are set forth in the following numbered clauses:

Clause 1. A method comprising: receiving, with an opening in a housing of a medical waste tracking device, a package for a medical device; determining, with a sensor of the medical waste tracking device, first identifying information from the package for the medical device; determining, with at least one processor, based on the first identifying information, that the medical device is in use; receiving, with the opening in the housing of the medical waste tracking device, the medical device; determining, with the sensor of the medical waste tracking device, second identifying information from the medical device; and determining, with at least one processor, based on the second identifying information, that the medical device is not in use.

Clause 2. The method of clause 1, further comprising: associating, with at least one processor, the medical waste tracking device with at least one of a room and a patient assigned to the room.

Clause 3. The method of any of clauses 1 and 2, wherein each of the first identifying information and the second identifying information includes a same unique device code.

Clause 4. The method of any of clauses 1-3, wherein the first identifying information is associated with a first time, and wherein the second identifying information is associated with a second time subsequent to the first time.

Clause 5. The method of any of clauses 1-4, wherein the first identifying information includes a first indicator indicating that the first identifying information is associated with the package for the medical device, and wherein the second identifying information includes a second indicator indicating that the second identifying information is associated with the medical device.

Clause 6. The method of any of clauses 1-5, wherein determining, with the sensor of the medical waste tracking device, the first identifying information from the package for the medical device includes reading the first identifying information from a first information element encapsulating the first identifying information, and wherein determining, with the sensor of the medical waste tracking device, the second identifying information from the medical device includes reading the second identifying information from a second information element encapsulating the second identifying information.

Clause 7. The method of any of clauses 1-6, wherein the sensor of the medical waste tracking device reads the first identifying information from the first information element and the second identifying information from the second information element via a short range wireless communication protocol.

Clause 8. The method of any of clauses 1-7, wherein the sensor of the medical waste tracking device includes at least one of the following: an optical sensor, an acoustic sensor, or any combination thereof, and wherein the sensor of the medical waste tracking device reads the first identifying information from the first information element and the second identifying information from the second information element with the at least one of the optical sensor and the acoustic sensor.

Clause 9. The method of any of clauses 1-8, further comprising: transmitting, with a wireless communication device of the medical waste tracking device, the first identifying information and the second identifying information to a computing device.

Clause 10. The method of any of clauses 1-9, further comprising: establishing, with the wireless communication device of the medical waste tracking device, a communication connection with the medical device before receiving the medical device with the opening in the housing of the medical waste tracking device; forwarding, with the wireless communication device of the medical waste tracking device, when the medical device is in use, information received from the medical device to the computing device.

Clause 11. The method of any of clauses 1-10, further comprising: determining, with at least one processor, based on the first identifying information and a current time, that an amount of time that the medical device is in use satisfies a threshold; and providing, with at least one processor, in response to determining that the amount of time that the medical device is in use satisfies the threshold, an alert to a user, wherein the alert includes a recommendation to at least one of remove and replace the medical device.

Clause 12. The method of any of clauses 1-11, further comprising: determining, with at least one processor, based on the first identifying information and the second identifying information, that an amount of time that the medical device was in use satisfies a threshold; and providing, with at least one processor, in response to determining that the amount of time that the medical device was in use satisfies the threshold, a prompt to a user, wherein the prompt includes a request for the user to input a reason for removal of the medical device.

Clause 13. The method of any of clauses 1-12, further comprising: determining, with at least one processor, based on at least one of the first identifying information and the second identifying information, that the medical device includes a catheter; determining, with at least one processor, based on the first identifying information and the second identifying information, that an amount of time that the catheter was in use satisfies a threshold; incrementing, with at least one processor, in response to determining that the amount of time that the catheter was in use satisfies the threshold, a count associated with a number of catheter insertion attempts for an insertion site of a patient.

Clause 14. The method of any of clauses 1-13, further comprising: determining, with a scale of the fluid waste tracking device, a weight of a fluid received via the opening in the housing; and determining, with at least one processor, an amount of fluid loss associated with a patient based on the weight of the fluid.

Clause 15. The method of any of clauses 1-14, further comprising: determining, with at least one processor, based on the second identifying information, a type of the medical device; and providing, with the at least one processor, based on the type of the medical device, a prompt to a user, wherein the prompt includes a request for the user to dispose of the medical device with a different medical waste tracking device.

Clause 16. The method of any of clauses 1-15, further comprising: determining, with at least one processor, based on the second identifying information, a type of the medical device; and depositing, with a sorting mechanism of the medical waste tracking device, based on the type of the medical device, the medical device into one of a plurality of receptacles.

Clause 17. The method of any of clauses 1-16, further comprising: disabling, with the medical waste tracking device, a communications capability of the medical device received in the opening in the housing of the medical waste tracking device.

Clause 18. The method of any of clauses 1-17, wherein the medical waste tracking device includes a first medical waste tracking device and a second medical waste tracking device, wherein the package for the medical device is received with the opening in the housing of the first medical waste tracking device, wherein the sensor of the first medical waste tracking device determines the first identifying information from the package for the medical device, wherein the medical device is received with the opening in the housing of the second medical waste tracking device, wherein the sensor of the second medical waste tracking device determines the second identifying information from the medical device, and wherein the method further comprises: establishing, with a wireless communication device of the first medical waste tracking device and a wireless communication device of the second medical waste tracking device, at least one of the following: (i) a communication connection between the wireless communication device of the first medical waste tracking device and the wireless communication device of the second medical waste tracking device, (ii) a communication connection between the wireless communication device of the first medical waste tracking device and a computing device and a communication connection between the wireless communication device of the second medical waste tracking device and the computing device, or any combination thereof.

Clause 19. The method of any of clauses 1-18, wherein the medical waste tracking device includes the one or more processors.

Clause 20. The method of any of clauses 1-19, wherein the one or more processors are included in a computing device external to the medical waste tracking device.

Clause 21. A system comprising: a medical waste tracking device including: a housing including an opening configured to receive a medical device and a package for the medical device; and a sensor configured to determine first identifying information from the package for the medical device and second identifying information from the medical device; and one or more processors programmed and/or configured to: determine, based on the first identifying information, that the medical device is in use; and determine, based on the second identifying information, that the medical device is not in use.

Clause 22. The system of clause 21, wherein the one or more processors are further programmed and/or configured to: associate the medical waste tracking device with at least one of a room and a patient assigned to the room.

Clause 23. The system of any of clauses 21 and 22, wherein each of the first identifying information and the second identifying information includes a same unique device code.

Clause 24. The system of any of clauses 21-23, wherein the first identifying information is associated with a first time, and wherein the second identifying information is associated with a second time subsequent to the first time.

Clause 25. The system of any of clauses 21-24, wherein the first identifying information includes a first indicator indicating that the first identifying information is associated with the package for the medical device, and wherein the second identifying information includes a second indicator indicating that the second identifying information is associated with the medical device.

Clause 26. The system of any of clauses 21-25, wherein the sensor is configured to determine the first identifying information from the package for the medical device by reading the first identifying information from a first information element encapsulating the first identifying information, and wherein the sensor is configured to determine the second identifying information from the medical device by reading the second identifying information from a second information element encapsulating the second identifying information.

Clause 27. The system of any of clauses 21-26, wherein the sensor is configured to read the first identifying information from the first information element and the second identifying information from the second information element via a short range wireless communication protocol.

Clause 28. The system of any of clause 21-27, wherein the sensor of the medical waste tracking device includes at least one of the following: an optical sensor, an acoustic sensor, or any combination thereof, and wherein the sensor is configured to read the first identifying information from the first information element and the second identifying information from the second information element with the at least one of the optical sensor and the acoustic sensor.

Clause 29. The system of any of clauses 21-28, wherein the medical waste tracking device further includes: a wireless communication device configured to transmit the first identifying information and the second identifying information to a computing device.

Clause 30. The system of any of clauses 21-29, wherein the wireless communication device is configured to establish a communication connection with the medical device before the medical device is received with the opening in the housing of the medical waste tracking device, and wherein the wireless communication device is configured to forward, when the medical device is in use, information received from the medical device to the computing device.

Clause 31. The system of any of clauses 21-30, wherein the one or more processors are further programmed and/or configured to: determine, based on the first identifying information and a current time, that an amount of time that the medical device is in use satisfies a threshold; and provide, in response to determining that the amount of time that the medical device is in use satisfies the threshold, an alert to a user, wherein the alert includes a recommendation to at least one of remove and replace the medical device.

Clause 32. The system of any of clauses 21-31, wherein the one or more processors are further programmed and/or configured to: determine, based on the first identifying information and the second identifying information, that an amount of time that the medical device was in use satisfies a threshold; and provide, in response to determining that the amount of time that the medical device was in use satisfies the threshold, a prompt to a user, wherein the prompt includes a request for the user to input a reason for removal of the medical device.

Clause 33. The system of any of clauses 21-32, wherein the one or more processors are further programmed and/or configured to: determine, based on at least one of the first identifying information and the second identifying information, that the medical device includes a catheter; determine, based on the first identifying information and the second identifying information, that an amount of time that the catheter was in use satisfies a threshold; increment, in response to determining that the amount of time that the catheter was in use satisfies the threshold, a count associated with a number of catheter insertion attempts for an insertion site of a patient.

Clause 34. The system of any of clauses 21-33, wherein the medical waste tracking device further includes a scale configured to determine a weight of a fluid received via the opening in the housing, and wherein the one or more processors are further programmed and/or configured to determine an amount of fluid loss associated with a patient based on the weight of the fluid.

Clause 35. The system of any of clauses 21-34, wherein the one or more processors are further programmed and/or configured to: determine, based on the second identifying information, a type of the medical device; and provide, based on the type of the medical device, a prompt to a user, wherein the prompt includes a request for the user to dispose of the medical device with a different medical waste tracking device.

Clause 36. The system of any of clauses 21-35, wherein the medical waste tracking device further includes: a sorting mechanism configured to deposit the medical device into one of a plurality of receptacles based on a type of the medical device, wherein the one or more processors are further programmed and/or configured to: determine, based on the second identifying information, the type of the medical device.

Clause 37. The system of any of clauses 21-36, wherein the medical waste tracking device is configured to disable a communications capability of the medical device received in the opening in the housing of the medical waste tracking device.

Clause 38. The system of any of clauses 21-37, further comprising: a further medical waste tracking device, wherein the medical waste tracking device and the further medical waste tracking device are configured to establish at least one of the following: (i) a communication connection between the medical waste tracking device and the further medical waste tracking device, (ii) a communication connection between the medical waste tracking device and a computing device and a communication connection between the further medical waste tracking device and the computing device, or any combination thereof.

Clause 39. The system of any of clauses 21-38, wherein the medical waste tracking device includes the one or more processors.

Clause 40. The system of any of clauses 21-39, further comprising: an external computing device including the one or more processors.

Clause 41. A medical waste tracking device comprising: a housing including an opening configured to receive a medical device and a package for the medical device; and a sensor configured to determine first identifying information from the package for the medical device and second identifying information from the medical device; and one or more processors programmed and/or configured to: determine, based on the first identifying information, that the medical device is in use; and determine, based on the second identifying information, that the medical device is not in use.

Clause 42. The medical waste tracking device of clause 41, further comprising: a receptacle configured to hold the medical device and the package for the medical device received with the opening in the housing.

Clause 43. The medical waste tracking device of any of clauses 41 and 42, wherein the receptacle is removably attached to the housing.

Clause 44. The medical waste tracking device of any of clauses 41-43, wherein the one or more processors are further programmed and/or configured to: determine, based on the first identifying information and a current time, that an amount of time that the medical device is in use satisfies a threshold; and provide, in response to determining that the amount of time that the medical device is in use satisfies the threshold, an alert to a user, wherein the alert includes a recommendation to at least one of remove and replace the medical device.

Clause 45. The medical waste tracking device of any of clauses 41-44, wherein the one or more processors are further programmed and/or configured to: determine, based on at least one of the first identifying information and the second identifying information, that the medical device includes a catheter; determine, based on the first identifying information and the second identifying information, that an amount of time that the catheter was in use satisfies a threshold; increment, in response to determining that the amount of time that the catheter was in use satisfies the threshold, a count associated with a number of catheter insertion attempts for an insertion site of a patient.

Clause 46. A method comprising: receiving, with an opening in a housing of a medical waste tracking device, a package for a medical device; determining, with a sensor of the medical waste tracking device, first identifying information from the package for the medical device; determining, with at least one processor, based on the first identifying information, that the medical device is in use; determining, with at least one processor, based on the first identifying information and a current time, that an amount of time that the medical device is in use satisfies a threshold; and providing, with at least one processor, in response to determining that the amount of time that the medical device is in use satisfies the threshold, an alert to a user, wherein the alert includes a recommendation to at least one of remove and replace the medical device and/or an indication of the amount of time that the medical device has been in use.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of limits. As used in the specification and the claims, the singular form of "a," "an," and "the" include plural referents unless the context clearly dictates otherwise.

BRIEF DESCRIPTION OF THE DRAWINGS

Additional advantages and details of embodiments or aspects of the present disclosure are explained in greater detail below with reference to the exemplary embodiments that are illustrated in the accompanying schematic figures, in which.

DETAILED DESCRIPTION

Figure 1A:
FIG. 1A is a diagram of non-limiting embodiments or aspects of an environment in which systems, devices, products, apparatus, and/or methods, described herein, can be implemented.
Figure 1A:
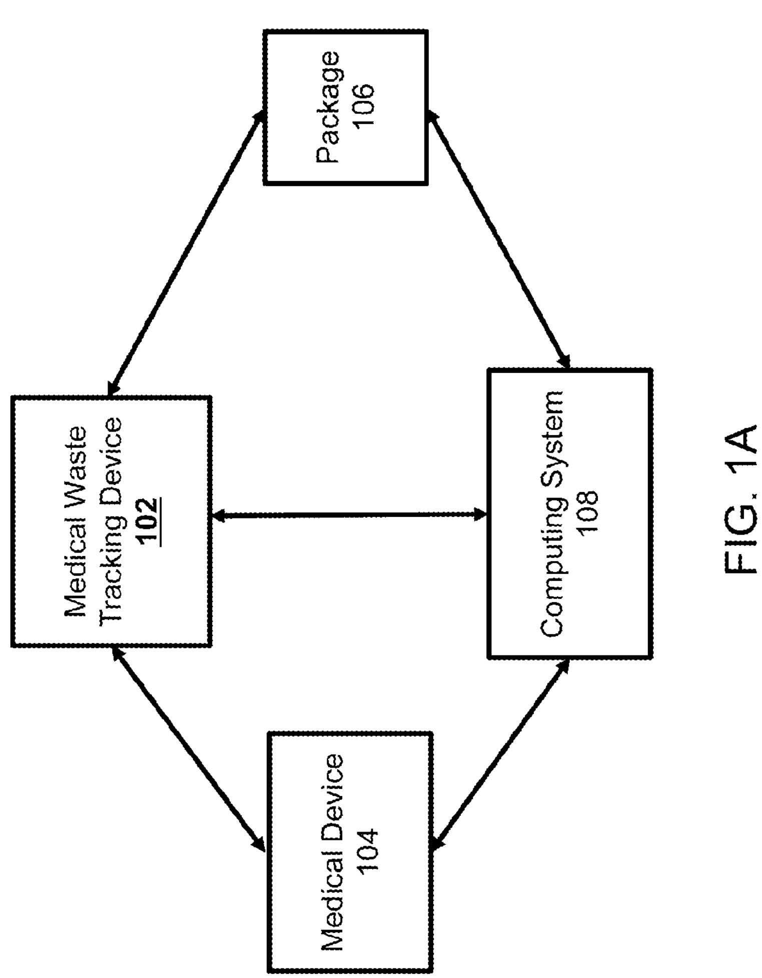

It is to be understood that the present disclosure may assume various alternative variations and step sequences, except where expressly specified to the contrary. It is also to be understood that the specific devices and processes illustrated in the attached drawings, and described in the following specification, are simply exemplary and non-limiting embodiments or aspects. Hence, specific dimensions and other physical characteristics related to the embodiments or aspects disclosed herein are not to be considered as limiting.

For purposes of the description hereinafter, the terms "end," "upper," "lower," "right," "left," "vertical," "horizontal," "top," "bottom," "lateral," "longitudinal," and derivatives thereof shall relate to the present disclosure as it is oriented in the drawing figures. However, it is to be understood that the present disclosure may assume various alternative variations and step sequences, except where expressly specified to the contrary. It is also to be understood that the specific devices and processes illustrated in the attached drawings, and described in the following specification, are simply exemplary embodiments or aspects of the present disclosure. Hence, specific dimensions and other physical characteristics related to the embodiments or aspects of the embodiments disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one." Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least in partially on" unless explicitly stated otherwise.

As used herein, the terms "communication" and "communicate" refer to the receipt or transfer of one or more signals, messages, commands, or other type of data. For one unit (e.g., any device, system, or component thereof) to be in communication with another unit means that the one unit is able to directly or indirectly receive data from and/or transmit data to the other unit. This may refer to a direct or indirect connection that is wired and/or wireless in nature. Additionally, two units may be in communication with each other even though the data transmitted may be modified, processed, relayed, and/or routed between the first and second unit. For example, a first unit may be in communication with a second unit even though the first unit passively receives data and does not actively transmit data to the second unit. As another example, a first unit may be in communication with a second unit if an intermediary unit processes data from one unit and transmits processed data to the second unit. It will be appreciated that numerous other arrangements are possible.

It will be apparent that systems and/or methods, described herein, can be implemented in different forms of hardware, software, or a combination of hardware and software. The actual specialized control hardware or software code used to implement these systems and/or methods is not limiting of the implementations. Thus, the operation and behavior of the systems and/or methods are described herein without reference to specific software code, it being understood that software and hardware can be designed to implement the systems and/or methods based on the description herein.

Some non-limiting embodiments or aspects are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

As used herein, the term "computing device" may refer to one or more electronic devices that are configured to directly or indirectly communicate with or over one or more networks. A computing device may be a mobile or portable computing device, a desktop computer, a server, and/or the like. Furthermore, the term "computer" may refer to any computing device that includes the necessary components to receive, process, and output data, and normally includes a display, a processor, a memory, an input device, and a network interface. A "computing system" may include one or more computing devices or computers. An "application" or "application program interface" (API) refers to computer code or other data sorted on a computer-readable medium that may be executed by a processor to facilitate the interaction between software components, such as a client-side front-end and/or server-side back-end for receiving data from the client. An "interface" refers to a generated display, such as one or more graphical user interfaces (GUIs) with which a user may interact, either directly or indirectly (e.g., through a keyboard, mouse, touchscreen, etc.). Further, multiple computers, e.g., servers, or other computerized devices directly or indirectly communicating in the network environment may constitute a "system" or a "computing system".

Referring now to FIG. 1A, FIG. 1A is a diagram of an example environment 100 in which devices, systems, methods, and/or products described herein, may be implemented. As shown in FIG. 1A, environment 100 includes medical waste tracking device 102, medical device 104, package 106, and/or computing system 108. Systems and/or devices of environment 100 can interconnect via wired connections, wireless connections, or a combination of wired and wireless connections. For example, systems and/or devices of environment 100 may interconnect via a cellular network (e.g., a long-term evolution (LTE) network, a third generation (3G) network, a fourth generation (4G) network, a fifth generation network (5G), a code division multiple access (CDMA) network, etc.), a public land mobile network (PLMN), a local area network (LAN), a wide area network (WAN), a metropolitan area network (MAN), a telephone network (e.g., the public switched telephone network (PSTN)), a private network, an ad hoc network, an intranet, the Internet, a fiber optic-based network, a cloud computing network, a short range wireless communication network, and/or the like, and/or any combination of these or other types of networks.

Medical waste tracking device 102 may include one or more devices capable of receiving information and/or data from one or more other medical waste tracking devices 102, medical device 104, package 106, and/or computing system 108 and/or communicating information and/or data to one or more other medical waste tracking devices 102, medical device 104, package 106, and/or computing system 108. For example, medical waste tracking device 102 may include one or more computing systems including one or more processors (e.g., one or more computing devices, one or more mobile computing devices, etc.).

In some non-limiting embodiments or aspects, medical waste tracking device 102 is capable of receiving information from one or more other medical waste tracking devices 102, medical device 104, package 106, and/or computing system 108 via a short range wireless communication connection (e.g., an NFC communication connection, an RFID communication connection, a Bluetooth® communication connection, and/or the like), and/or communicating information to one or more other medical waste tracking devices 102, medical device 104, package 106, and/or computing system 108 via a short range wireless communication connection. In some non-limiting embodiments or aspects, medical waste tracking device 102 is capable of receiving information from one or more other medical waste tracking devices 102, medical device 104, package 106, and/or computing system 108 via a long range wireless communication connection (e.g., a Wi-Fi communication connection, a cellular communication connection, and/or the like), and/or communicating information to one or more other medical waste tracking devices 102, medical device 104, package 106, and/or computing system 108 via a long range wireless communication connection Further details regarding non-limiting embodiments or aspects of medical waste tracking device 102 are provided below with regard to FIG. 2.

Medical device 104 may include a connector (e.g., a needless connector, etc.), a catheter (e.g., a peripherally inserted central catheter (PICC), a peripheral intravenous catheter (PIVC), a central venous catheter (CVC), etc.), tubing, a disinfecting cap, and/or the like. In some non-limiting embodiments or aspects, medical device 104 may include one or more sensors configured to sense information and/or data associated with medical device 104, a fluid flowing through and/or adjacent to medical device 104, a patient, and/or the like. In some non-limiting embodiments or aspects, medical device 104 may include a smart device as described in International Application Nos. PCT/US20/16539 and PCT/US20/16546, each of which were filed Feb. 4, 2020, the entire contents of each of which are hereby incorporated by reference.

Medical device 104 may include one or more devices capable of receiving information and/or data from medical waste tracking device 102, one or more other medical devices 104, package 106, and/or computing system 108 and/or communicating information and/or data to medical waste tracking device 102, one or more other medical devices 104, package 106, and/or computing system 108. For example, medical device 104 may include one or more computing systems including one or more processors (e.g., one or more computing devices, one or more mobile computing devices, etc.).

In some non-limiting embodiments or aspects, medical device 104 is capable of receiving information from medical waste tracking device 102, one or more other medical devices 104, package 106, and/or computing system 108 via a short range wireless communication connection (e.g., an NFC communication connection, an RFID communication connection, a Bluetooth® communication connection, and/or the like), and/or communicating information to medical waste tracking device 102, one or more other medical devices 104, package 106, and/or computing system 108 via a short range wireless communication connection. In some non-limiting embodiments or aspects, medical device 104 is capable of receiving information from medical waste tracking device 102, one or more other medical devices 104, package 106, and/or computing system 108 via a long range wireless communication connection (e.g., a Wi-Fi communication connection, a cellular communication connection, and/or the like), and/or communicating information to medical waste tracking device 102, one or more other medical devices 104, package 106, and/or computing system 108 via a long range wireless communication connection Further details regarding non-limiting embodiments or aspects of medical device 104 are provided below with regard to FIG. 1B.

Package 106 may include a package (e.g., a box, a carton, a sleeve, a bag, etc.) for medical device 104. For example, package 106 may provide a sealed, sterile, and/or bacteria free environment for storing and/or transporting medical device 104. As an example, package 106 may be opened and medical device 104 may be removed from package 106 immediately prior to use of medical device 104.

Package 106 may include one or more devices capable of receiving information and/or data from medical waste tracking device 102, medical device 104, and/or computing system 108 and/or communicating information and/or data to medical waste tracking device 102, medical device 104, and/or computing system 108. For example, package 106 may include one or more computing systems including one or more processors (e.g., one or more computing devices, one or more mobile computing devices, etc.).

In some non-limiting embodiments or aspects, package 106 is capable of receiving information from medical waste tracking device 102, medical device 104, and/or computing system 108 via a short range wireless communication connection (e.g., an NFC communication connection, an RFID communication connection, a Bluetooth® communication connection, and/or the like), and/or communicating information to medical waste tracking device 102, medical device 104, and/or computing system 108 via a short range wireless communication connection.

Further details regarding non-limiting embodiments or aspects of package 106 are provided below with regard to FIG. 1B.

Computing system 108 may include one or more devices capable of receiving information and/or data from medical waste tracking device 102, medical device 104, and/or package 106 and/or communicating information and/or data to medical waste tracking device 102, medical device 104, and/or package 106. For example, computing system 108 may include one or more computing systems including one or more processors (e.g., one or more computing devices, one or more mobile computing devices, etc.). In some non-limiting embodiments or aspects, computing system 108 includes a secure hospital server and/or one or more secure hospital databases that store personally identifiable information (PII) and/or Health Insurance Portability and Accountability Act (HIPAA) protected information. In some non-limiting embodiments or aspects, computing system 108 includes a nurse station in a hospital. For example, computing system 108 may provide bedside nurse support, nursing station manager support, retrospective reporting for nursing administration, and/or the like.

Figure 1B:
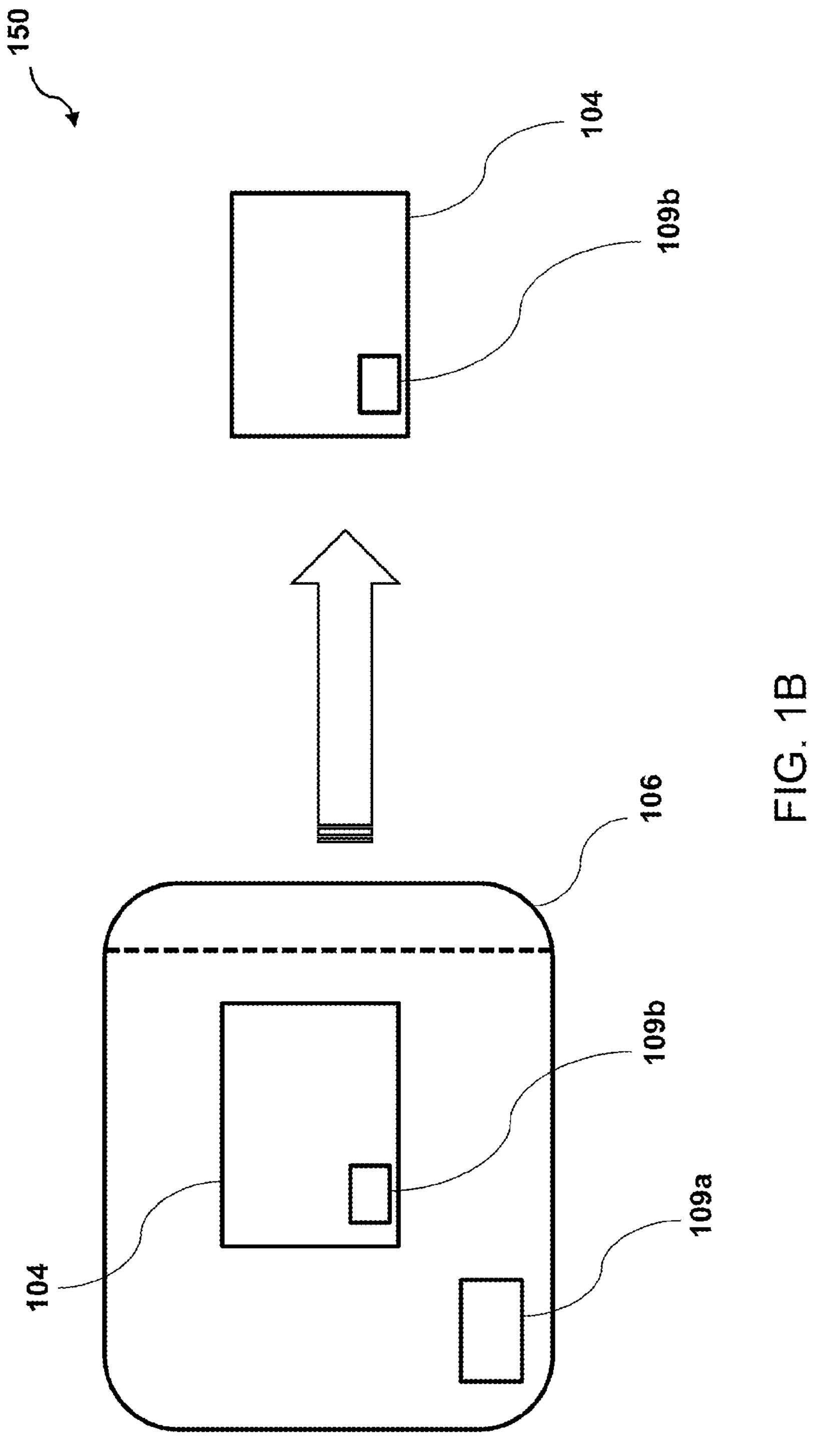
FIG. 1B is diagram of non-limiting embodiments or aspects of an implementation of one or more systems and/or one or more devices of FIG. 1A.

Referring now to FIG. 1B, FIG. 1B is a diagram of non-limiting embodiments or aspects of an implementation 150 of one or more systems and/or one or more devices of FIG. 1A. As shown in FIG. 1B, package 106 may include (e.g., house, encompass, etc.) medical device 104. Package 106 may be opened to remove medical device 104 for use. Package 106 may include first information element 109*a*, and medical device 104 may include second information 109*b*. An information element may include at least one of the following: a computing device, a microcontroller, a wireless communication device, an RFID tag, an NFC tag, a Bluetooth® chip, a barcode (e.g., a 2D barcode, a 3D barcode, a QR code, etc.), a label including an optical pattern and/or a mechanical pattern (e.g., braille, etc.), an audio output device (e.g., that outputs an auditory signal having a unique sound signature, etc.), an optical output device (e.g., that provides an LED light pattern, etc.), or any other machine readable identifier (e.g., a size and shape of a housing of package 106 and/or a housing of medical device 104 identifiable via image processing of an image of the housing, etc.). An information element may be attached to an external surface of a device, integrated with a device (e.g., within a housing of the device, etc.), and/or be provided by one or more components of a computing device that performs other functions of the device.

First information element 109*a* may encapsulate first identifying information associated with medical device 104 and/or package 106 for medical device 104, and second information element 109*b* may encapsulate second identifying information associated with medical device 104 and/or package 106 for medical device 104. For example, each of the first identifying information and the second identifying information may include a same unique device code (e.g., a unique device code associated with medical device 104 included in package 106, etc.). In some non-limiting embodiments or aspects, the first identifying information includes a first indicator indicating that the first identifying information is associated with the package for the medical device, and/or the second identifying information includes a second indicator indicating that the second identifying information is associated with the medical device. In some non-limiting embodiments or aspects, the first identifying information is automatically associated with a first time (e.g., a first time stamp, etc.) when that information is read from or provided by first information element 109*a*, and the second identifying information is automatically associated with a second time (e.g., a second time stamp, etc.) when that information is read from or provided by second information element 109*b*. In some non-limiting embodiments or aspects, the first identifying information and/or the second identifying information are associated with a type of medical device 104 (e.g., a catheter, a connector, a type of catheter, a type of connector, intended use with a hazardous vs. non-hazardous material, etc.).

Figure 2:
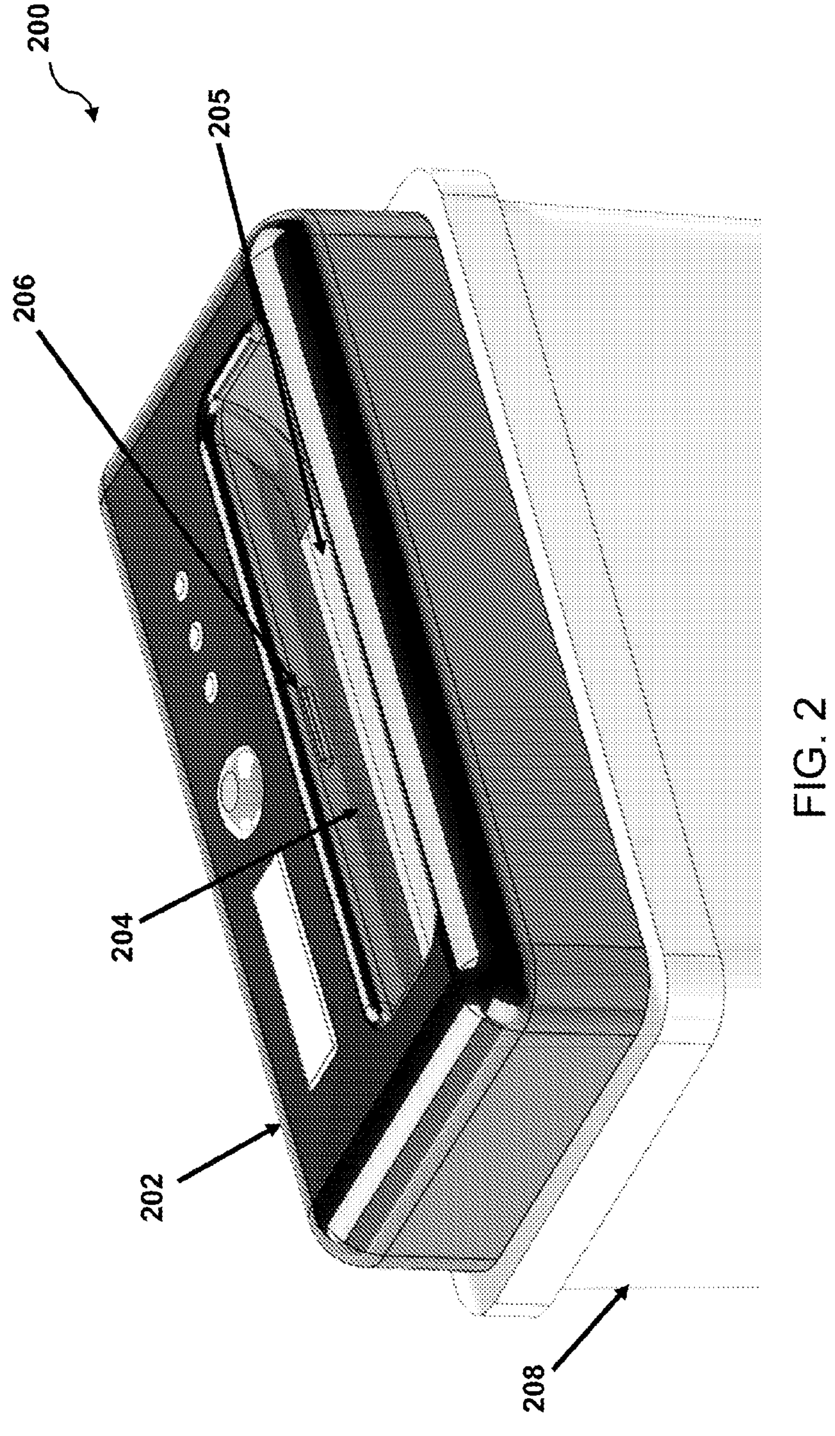
FIG. 2 is a diagram of non-limiting embodiments or aspects of an implementation of one or more systems and/or one or more devices of FIG. 1A.

Referring now to FIG. 2, FIG. 2 is a diagram of non-limiting embodiments or aspects of an implementation 200 of one or more systems and/or one or more devices of FIG. 1A. As shown in FIG. 2, medical waste tracking device 102 may include housing 202 including opening 204 configured to receive medical device 104 and package 106 and/or sensor 206.

Sensor 206 may be configured to determine the first identifying information from package 106 and the second identifying information from medical device 104. For example, sensor 206 may be configured to automatically read, access, and/or establish a communication connection with an information element in response to a package or a medical device including that information element being received in opening 204 of housing 202. Sensor 206 may include at least one of the following: a short range wireless communication reader (e.g., an RFID reader, an NFC reader, a Bluetooth® reader, etc.), an optical sensor (e.g., a barcode scanner, an image capture device including imaging processing software configured to identify a device and/or identifying information associated therewith via image processing of an image of a housing of the device, an acoustic sensor, or any combination thereof.

As further shown in FIG. 2, housing 202 may be attached to (e.g., removably attached to, etc.) and/or integrated with receptacle 208. Receptacle 208 may be configured to hold medical device 104 and/or package 106 that are received in opening 204 of housing 202. In some non-limiting embodiments or aspects, opening 204 may include a base 205 configured to move (e.g., slide open, rotate open, etc.) to connect opening 204 to an interior of receptacle 208. For example, base 205 may be configured to automatically open to allow medical device 104 or package 106 in opening 204 to fall into receptacle 208 in response to sensor 206 determining the first identifying information from package 106 or the second identifying information from medical device 104. However, non-limiting embodiments or aspects are not limited thereto, and base 205 may be omitted, with a path between opening 204 and an interior of receptacle 208 always in place. Housing 202 may be attached to any form of receptacle, such as receptacles for basic garbage, recyclables, hazardous waste, sharps containers, soiled waste, battery disposal, and/or the like. Medical waste tracking device 102 may be a durable and/or reusable device, or medical waste tracking device may be a disposable device.

In some non-limiting embodiments or aspects, housing 202 includes a user interface (e.g., input component 310, output component 312, a display, buttons, signal and/or device status indicator lights, etc.) configured to receive user input from a user and/or provide information and/or data (e.g., alerts, prompts, etc.) to the user. In some non-limiting embodiments or aspects, housing 202 may include a battery (not shown), such as a rechargeable battery, a replaceable battery, a disposable battery, and/or the like, configured to provide power for operating one or more components of medical waste tracking device 102. In some non-limiting embodiments or aspects, housing 202 may include a processor (e.g., processor 304, a low power microcontroller (MCU), etc.) configured to determine, based on the first identifying information, that medical device is in use 104 and/or determine, based on the second identifying information, that medical device 104 is not in use, as is described in more detail herein with respect to FIGS. 4-8.

In some non-limiting embodiments or aspects, housing 202 includes a wireless communication device (e.g., communication interface 314, etc.) configured to establish a communication connection with medical device 104 before medical device 104 is received in opening 204 of housing 206, and the wireless communication device may be configured to automatically forward, when medical device 104 is in use, information received from medical device 104 to computing system 108. For example, medical waste tracking device 102 may act as an information hub, gateway, and/or signal booster for forwarding patient specific data captured by medical device 104 to one or more other devices (e.g., computing system 108, etc.).

In some non-limiting embodiments or aspects, housing 202 includes a sorting mechanism configured to deposit medical device 104 (and/or package 106) into one of a plurality of receptacles based on a type of the medical device (and/or a type of package 106). For example, base 205 may move (e.g., slide open, rotate open, etc.) in a first direction to allow medical device 104 or package 106 in opening 204 to fall into a first side or subdivision of receptacle 208, and base 205 may move (e.g., slide open, rotate open, etc.) in a second direction to allow medical device 104 or package 106 in opening 204 to fall into a second side or subdivision of receptacle 208. In some non-limiting embodiments or aspects, the sorting mechanism may remove a battery from medical device 104. As an example, medical device 104 may include an ejection button or an insertion point such that when directionally oriented and inserted into the sorting mechanism via opening 204 movement through the opening 204 and interaction with the housing 202 surrounding the opening ejects the battery into an adjacent chamber, or alternatively, as medical device 104 passes through opening 204 it is automatically forced to become aligned to facilitate the removal of the battery (e.g., by compression of the ejection button to eject the battery or by a mechanical interface to remove battery as it passes deeper into the waste receptacle, etc.).

In some non-limiting embodiments or aspects, medical waste tracking device 102 is configured to disable a communications capability of medical device 104 (and/or package 106) received in opening 204 in housing 202 of medical waste tracking device 102. For example, medical waste tracking device 102 may be configured to wirelessly communicate with second information element 109*b* and/or medical device 104 to control second information element 109*b* and/or medical device 104 (and/or first information element 109*a* and/or package 106) to prevent or disable communication therefrom. As another example, medical waste tracking device 102 (e.g., housing 202, receptacle 208, etc.) may be formed of a material that blocks a wireless communication signal from second information element 109*b* and/or medical device 104 (and/or first information element 109*a* and/or package 106). In some non-limiting embodiments or aspects, medical waste tracking device 102 may determine that medical device 104 is no longer in use based on a loss of signal from and/or communications with medical device 104 (e.g., medical waste tracking device 102 may determine that medical device 104 is no longer in use in response to not sensing any signals from either the packaging or the device, which may serve as a signal to a different communication (e.g., computing device 108, etc.) set to disable further communication from medical device 104 and thereby turn off or power down medical device 104

The number and arrangement of devices and systems shown in FIGS. 1A, 1B, and 2 is provided as an example. There may be additional devices and/or systems, fewer devices and/or systems, different devices and/or systems, or differently arranged devices and/or systems than those shown in FIGS. 1A, 1B, and 2. Furthermore, two or more devices and/or systems shown in FIGS. 1A, 1B, and 2 may be implemented within a single device and/or system, or a single device and/or system shown in FIGS. 1A, 1B, and 2 may be implemented as multiple, distributed devices and/or systems. Additionally, or alternatively, a set of devices and/or systems (e.g., one or more devices or systems) of environment 100 may perform one or more functions described as being performed by another set of devices and/or systems of environment 100.

Figure 3:
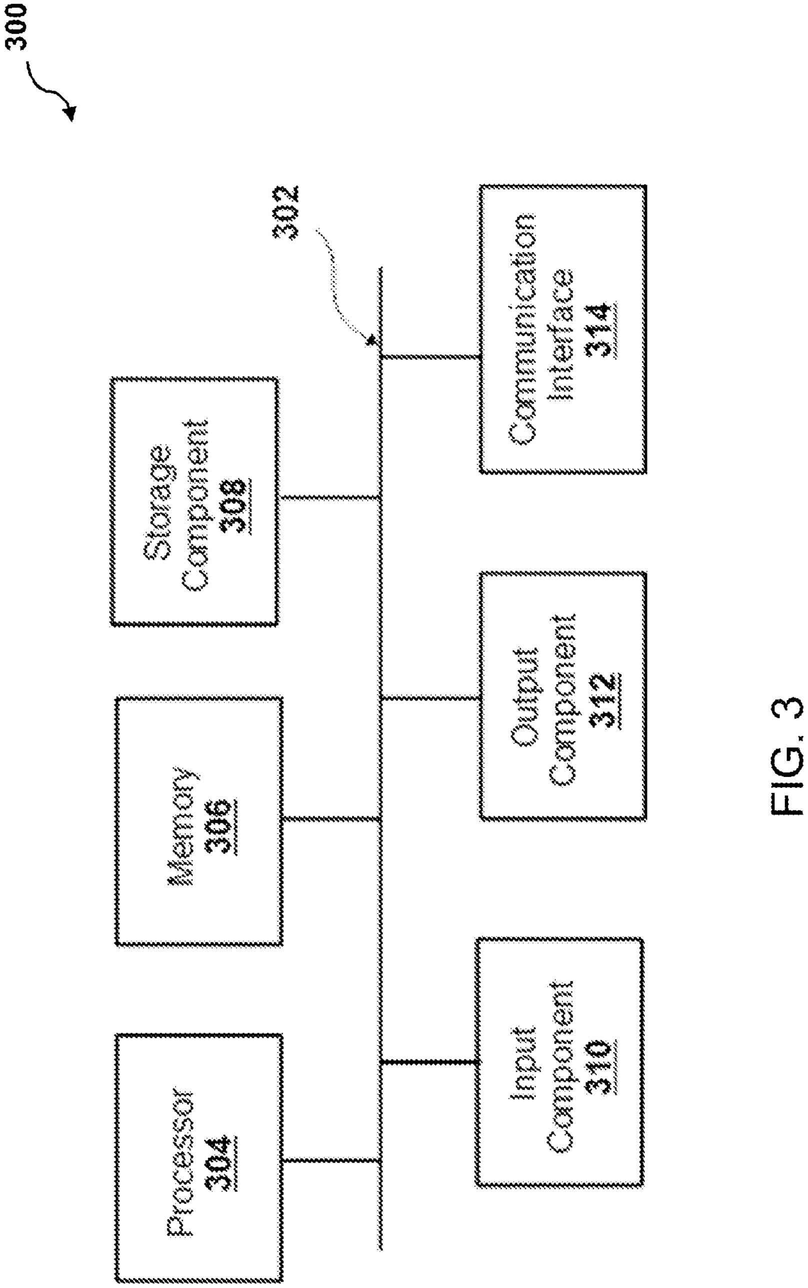
FIG. 3 is a diagram of non-limiting embodiments or aspects of components of one or more devices and/or one or more systems of FIGS. 1A, 1B, and 2.

Referring now to FIG. 3, FIG. 3 is a diagram of example components of a device 300. Device 300 may correspond to medical waste tracking device 102, medical device 104, package 106, and/or one or more devices of computing system 108. In some non-limiting embodiments or aspects, medical waste tracking device 102, medical device 104, package 106, and/or one or more devices of computing system 108 can include at least one device 300 and/or at least one component of device 300. As shown in FIG. 3, device 300 may include a bus 302, a processor 304, memory 306, a storage component 308, an input component 310, an output component 312, and a communication interface 314.

Bus 302 may include a component that permits communication among the components of device 300. In some non-limiting embodiments or aspects, processor 304 may be implemented in hardware, firmware, or a combination of hardware and software. For example, processor 304 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), a microcontroller (MCU), etc.) that can be programmed to perform a function. Memory 306 may include random access memory (RAM), read only memory (ROM), and/or another type of dynamic or static storage device (e.g., flash memory, magnetic memory, optical memory, etc.) that stores information and/or instructions for use by processor 304.

Storage component 308 may store information and/or software related to the operation and use of device 300. For example, storage component 308 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 310 may include a component that permits device 300 to receive information, such as via user input (e.g., a touch screen display, a keyboard, a keypad, a mouse, a button, a switch, a microphone, a camera, an electroencephalogram (EEG) monitor, etc.). Additionally, or alternatively, input component 310 may include a sensor for sensing information (e.g., a global positioning system (GPS) component, an accelerometer, a gyroscope, an actuator, etc.). Output component 312 may include a component that provides output information from device 300 (e.g., a display, a speaker, one or more light-emitting diodes (LEDs), and/or the like).

Communication interface 314 may include a transceiver-like component (e.g., a transceiver, a separate receiver and transmitter, etc.) that enables device 300 to communicate with other devices, such as via a wired connection, a wireless connection, or a combination of wired and wireless connections. Communication interface 314 may permit device 300 to receive information from another device and/or provide information to another device. For example, communication interface 314 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 300 may perform one or more processes described herein. Device 300 may perform these processes based on processor 304 executing software instructions stored by a computer-readable medium, such as memory 306 and/or storage component 308. A computer-readable medium (e.g., a non-transitory computer-readable medium) is defined herein as a non-transitory memory device. A non-transitory memory device includes memory space located inside of a single physical storage device or memory space spread across multiple physical storage devices.

Software instructions may be read into memory 306 and/or storage component 308 from another computer-readable medium or from another device via communication interface 314. When executed, software instructions stored in memory 306 and/or storage component 308 may cause processor 304 to perform one or more processes described herein. Additionally or alternatively, hardwired circuitry may be used in place of or in combination with software instructions to perform one or more processes described herein. Thus, embodiments or aspects described herein are not limited to any specific combination of hardware circuitry and software.

Memory 306 and/or storage component 308 may include data storage or one or more data structures (e.g., a database, etc.). Device 300 may be capable of receiving information from, storing information in, communicating information to, or searching information stored in the data storage or one or more data structures in memory 306 and/or storage component 308. For example, the information may input data, output data, medical data, or any combination thereof.

The number and arrangement of components shown in FIG. 3 are provided as an example. In some non-limiting embodiments or aspects, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
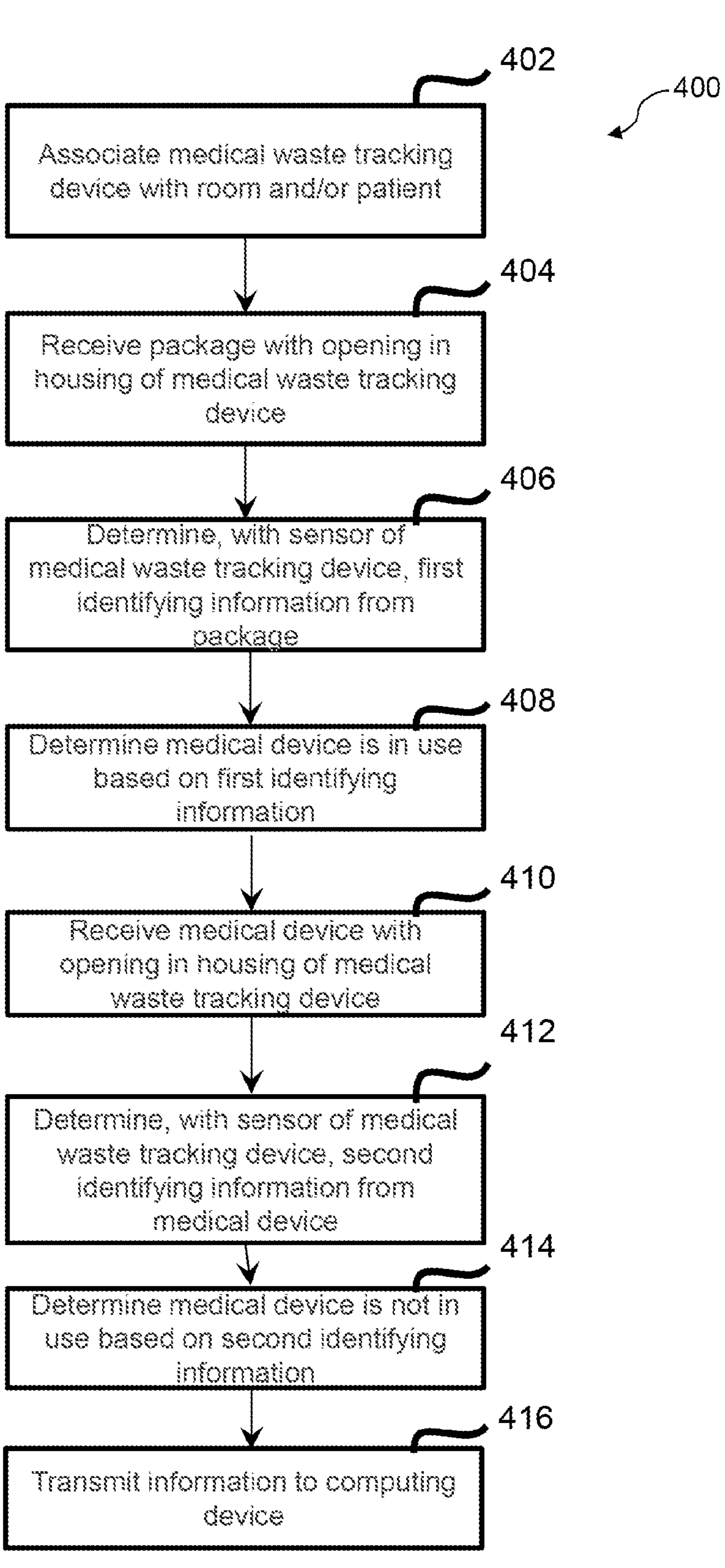
FIG. 4 is a flowchart of non-limiting embodiments or aspects of a process for medical waste tracking.

Referring now to FIG. 4, FIG. 4 is a flowchart of non-limiting embodiments or aspects of a process 300 for medical waste tracking. In some non-limiting embodiments or aspects, one or more of the steps of process 400 may be performed (e.g., completely, partially, etc.) by medical waste tracking device 102. In some non-limiting embodiments or aspects, one or more of the steps of process 400 may be performed (e.g., completely, partially, etc.) by another device or a group of devices separate from or including medical waste tracking device 102, such as computing system 108 (e.g., one or more devices of computing system 108).

As shown in FIG. 4, at step 402, process 400 includes associating a medical waste tracking device with at least one of a room and a patient assigned to the room. For example, medical waste tracking device 102 may associate medical waste tracking device 102 with at least one of a room and a patient assigned to the room (e.g., to a room and/or a patient assigned to the room in which medical waste tracking device 102 is located, etc.). Additionally, or alternatively, medical waste tracking device 102 may associate medical waste tracking device 102 with a clinician (e.g., with a clinician ID badge via a wireless communication protocol, etc.). For example, medical waste tracking device 102 may sense a nearest clinician ID badge and associate medical waste tracking device 102 with the clinician associated with the nearest clinician ID badge. As an example, medical waste tracking device 102 may provide a prompt to a user for the clinician associated with the nearest clinician ID badge to verify or confirm a patient associated with the medical waste tracking device 102 and/or a disposable of medical waste.

As shown in FIG. 4, at step 404, process 400 includes receiving, with an opening in a housing of a medical waste tracking device, a package for a medical device. For example, medical waste tracking device 102 may receive, with opening 204 of housing 202, package 106 for medical device 104. As an example, a user (e.g., a clinician, etc.) may dispose of or discard package 106 for medical device 104 in medical waste tracking device 102.

As shown in FIG. 4, at step 406, process 400 includes determining, with a sensor of a medical waste tracking device, first identifying information from a package for a medical device. For example, medical waste tracking device 106 may determine, with sensor 206, first identifying information from package 106 for medical device 104.

In some non-limiting embodiments or aspects, medical waste tracking device 102 determines, with sensor 206, the first identifying information from package 106 for medical device 104 by reading the first identifying information from first information element 109*a* encapsulating the first identifying information, and/or medical waste tracking device 102 determines, with sensor 206, the second identifying information from medical device 104 by reading the second identifying information from a second information element 109*b* encapsulating the second identifying information. For example, first information element 109*a* may be attached to and/or integrated with package 106 and/or second information element 109*b* may be attached to and/or integrated with medical device 104. As an example, sensor 206 of medical waste tracking device 102 may read the first identifying information from first information element 109*a* and/or the second identifying information from second information element 109*b* via a short range wireless communication protocol. As an example, sensor 206 of medical waste tracking device 102 may at least one of the following: an optical sensor, an acoustic sensor, or any combination thereof, and sensor 206 may read the first identifying information from first information element 109*a* and the second identifying information from second information element 109*b* with the at least one of the optical sensor and the acoustic sensor.

As shown in FIG. 4, at step 408, process 400 includes determining, based on first identifying information, that a medical device is in use. For example, medical waste tracking device 102 may determine, based on the first identifying information, that medical device 104 is in use (e.g., in the course of being placed and/or used for treatment of a patient, not yet discarded, etc.).

In some non-limiting embodiments or aspects, medical waste tracking device 102 (e.g., communication interface 314 of medical waste tracking device 102, etc.) may establish a communication connection with medical device 104 while medical device 104 is in use (e.g., before receiving medical device 104 with opening 204 in housing 202, etc.), and forward information received from medical device 104 to computing system 108. For example, medical waste tracking device 102 may act as an information hub, gateway, and/or signal booster for forwarding patient specific data captured by medical device 104 while medical device 104 is in use to one or more other devices (e.g., computing system 108, etc.).

Further details regarding non-limiting embodiments or aspects of step 408 of process 400 are provided below with regard to FIGS. 5 and 6.

As shown in FIG. 4, at step 410, process 400 includes receiving, with an opening in a housing of a medical waste tracking device, a medical device. For example, medical waste tracking device 102 may receive, with opening 204 in housing 202, medical device 104. As an example, a user (e.g., a clinician, etc.) may dispose of or discard medical device 104 in medical waste tracking device 102.

As shown in FIG. 4, at step 412, process 400 includes determining, with a sensor of a medical waste tracking device, second identifying information from a medical device. For example, medical waste tracking device 102 may determine, with sensor 206, second identifying information from medical device 104.

In some non-limiting embodiments or aspects, medical waste tracking device 102 includes a first medical waste tracking device and a second medical waste tracking device. For example, package 106 for medical device 104 may be received with the opening in the housing of the first medical waste tracking device, and the sensor of the first medical waste tracking device may determine the first identifying information from the package for the medical device. As an example, medical device 104 may be received with the opening in the housing of the second medical waste tracking device, and the sensor of the second medical waste tracking device may determine the second identifying information from medical device 104. In such an example, a wireless communication device of the first medical waste tracking device and a wireless communication device of the second medical waste tracking device may establish at least one of the following: (i) a communication connection between the wireless communication device of the first medical waste tracking device and the wireless communication device of the second medical waste tracking device, (ii) a communication connection between the wireless communication device of the first medical waste tracking device and computing system 108 and a communication connection between the wireless communication device of the second medical waste tracking device and computing system 108, or any combination thereof. In such an example, multiple medical waste tracking devices 102 on a same network may work together to identify linked events at different disposal medical waste tracking devices/receptacles (e.g. package disposal into basic waste and hazardous waste disposal into hazardous waste containers, etc.).

As shown in FIG. 4, at step 414, process 400 includes determining based on second identifying information, that a medical device is not in use. For example, medical waste tracking device 102 may determine, based on the second identifying information, that medical device 104 is not in use (e.g., not in the course of being placed and/or used for treatment of a patient, has been discarded, etc.).

In some non-limiting embodiments or aspects, medical waste tracking device 102 may disable (e.g., automatically disable, etc.) a communications capability of medical device 104 received in opening 204 in housing 202 of medical waste tracking device 102. For example, medical waste tracking device 102 may automatically establish wireless communications (e.g., in response to receipt of medical device 104 in opening 204 in housing 202 of medical waste tracking device 102, etc.) with second information element 109*b* and/or medical device 104 to control second information element 109*b* and/or medical device 104 (and/or first information element 109*a* and/or package 106) to prevent or disable communication therefrom. As another example, medical waste tracking device 102 (e.g., housing 202, receptacle 208, etc.) may be formed of a material that blocks a wireless communication signal from second information element 109*b* and/or medical device 104 (and/or first information element 109*a* and/or package 106).

In some non-limiting embodiments or aspects, medical waste tracking device 102 may determine, based on the second identifying information, a type of medical device 104 (e.g., a catheter, a connector, a type of catheter, a type of connector, a manufacturer, use with a hazardous vs. non-hazardous material, etc.). For example, medical waste tracking device 102 may provide based on the type of medical device 104, a prompt to a user, the prompt including a request for the user to dispose of the medical device with a different medical waste tracking device. As an example, if medical waste tracking device 102 is associated with a receptacle for non-hazardous waste disposal, and medical waste tracking device 102 determines that medical device 104 that a user is attempting to dispose of in medical waste tracking device 102 is associated with hazardous materials, medical waste tracking device 102 may direct the user or dispose of medical device 102 at different medical waste tracking device 102 or receptacle. In some non-limiting embodiments or aspects, medical waste tracking device 102 may use a sorting mechanism to automatically deposit medical device 104 into one of a plurality of receptacles attached to medical waste tracking device 102 based on the type of medical device 104.

Further details regarding non-limiting embodiments or aspects of step 414 of process 400 are provided below with regard to FIGS. 7 and 8.

As shown in FIG. 4, at step 416, process 400 includes transmitting information to a computing device. For example, medical waste tracking device 102 (e.g., communication interface 314 of medical waste tracking device 102, etc.) may transmit information and/or data (e.g., first identifying information, second identifying information, medical device in use state, failed insertion count, reason for device removal, issued alerts, etc.) to computing system 108. As an example, medical waste tracking device 102 and/or computing system 108 may analyze the information to determine medical device in use state, billing information (e.g., a billing amount associated with the use of medical device 104, etc.), failed catheter insertion attempts, monitor compliance for appropriate disposal of medical device 104 (e.g., determine whether chemo-associated medical devices are disposed of in appropriate disposal bins to determine appropriate handling and disposal processing, etc.), provide alerts and/or prompts to a user, and/or the like. In some non-limiting embodiments or aspects, medical waste tracking device 102 and/or computing system 108 may provide the information and/or analysis thereof to higher level computing systems and/or directly to a clinician or health care worker to provide a notification or alert associated with a medical device expiration and/or a dwell-time limit for a medical device based on a time of package disposal to a time of medical device disposal (or lack thereof).

Figure 5:
FIG. 5 is a flowchart of non-limiting embodiments or aspects of a process for medical waste tracking.
Figure 5:
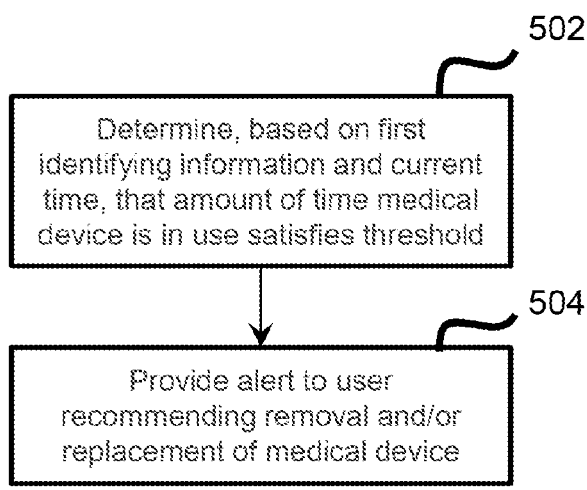

Referring now to FIG. 5, FIG. 5 is a flowchart of non-limiting embodiments or aspects of a process 500 for medical waste tracking. In some non-limiting embodiments or aspects, one or more of the steps of process 500 may be performed (e.g., completely, partially, etc.) by medical waste tracking device 102. In some non-limiting embodiments or aspects, one or more of the steps of process 500 may be performed (e.g., completely, partially, etc.) by another device or a group of devices separate from or including medical waste tracking device 102, such as computing system 108 (e.g., one or more devices of computing system 108).

As shown in FIG. 5, at step 502, process 500 includes determining, based on first identifying information and a current time, that an amount of time a medical device is in use satisfies a threshold. For example, medical waste tracking device 102 may determine based on the first identifying information (e.g., a time stamp associated with the first identifying information, etc.) and a current time, that an amount of time that the medical device is in use satisfies a threshold. As an example, medical waste tracking device 102 may determine whether a dwell time of medical device 104 is approaching and/or exceeds an allowed dwell time for medical device 104.

As shown in FIG. 5, at step 504, process 500 includes providing, in response to determining that an amount of time that a medical device is in use satisfies a threshold, an alert to a user, the alert including a recommendation to at least one of remove and replace the medical device. For example, medical waste tracking device 102 may provide, in response to determining that the amount of time that medical device 104 is in use satisfies the threshold, an alert to a user (e.g., via output component 312 of medical device 102, etc.), the alert including a recommendation to at least one of remove and replace medical device 104. As an example, medical waste tracking device 102 may alert a user when a dwell time of medical device 104 is nearing and/or past an allowed dwell time for medical device 104.

Figure 6:
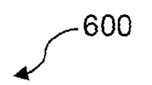
FIG. 6 is a flowchart of non-limiting embodiments or aspects of a process for medical waste tracking.
Figure 6:
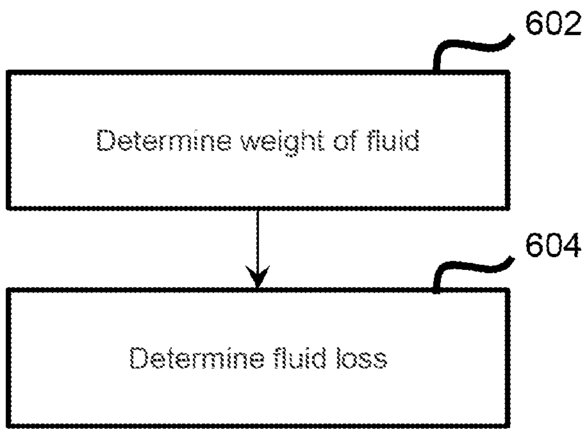

Referring now to FIG. 6, FIG. 6 is a flowchart of non-limiting embodiments or aspects of a process 600 for medical waste tracking. In some non-limiting embodiments or aspects, one or more of the steps of process 600 may be performed (e.g., completely, partially, etc.) by medical waste tracking device 102. In some non-limiting embodiments or aspects, one or more of the steps of process 600 may be performed (e.g., completely, partially, etc.) by another device or a group of devices separate from or including medical waste tracking device 102, such as computing system 108 (e.g., one or more devices of computing system As shown in FIG. 6, at step 602, process 600 includes determining a weight of a fluid received via an opening in a housing of a medical waste tracking device. For example, medical waste tracking device 102 may determine a weight of a fluid received via opening 204 in housing 202. As an example, medical waste tracking device 102 may include a built-in scale to momentarily delay disposal of and/or capture and/or measure a weight of medical device 104 and compare the measured weight of medical device 104 to a known weight of medical device 104 to determine an amount of fluid remaining in medical device 104 and, thus, the weight of the fluid received via opening 204 in housing 2020, providing a benefit to diversion prevention and/or detection of fluid loss associated with the patient. In some non-limiting embodiments or aspects, medical waste tracking device 102 may include a separate fluid port (not shown) via which any remaining fluid in medical device 104 is wasted and measured before disposable medical device 104 is completed. For example, medical waste tracking device may include a dual chamber receptacle with an area for liquid waste and another area for solid waste (e.g., medical device 104, etc.). In some non-limiting embodiments or aspects, a user may measure and dispose of any fluid remaining in medical device 104 and thereafter input the fluid measurement to medical waste tracking device 102 and dispose of medical device 104 via medical waste tracking device 102.

As show in FIG. 6, at step 604, process 600 includes determining a fluid loss associated with a patient. For example, medical waste tracking device 102 may determine an amount of fluid loss associated with the patient. As an example, medical waste tracking device may capture am event of fluid entry into disposal from drug loss during priming or like events (foreseen as entry point of liquid to be acknowledged at base function with increasing functionality to volume measurement and drug administration linkage).

Figure 7:
FIG. 7 is a flowchart of non-limiting embodiments or aspects of a process for medical waste tracking.
Figure 7:
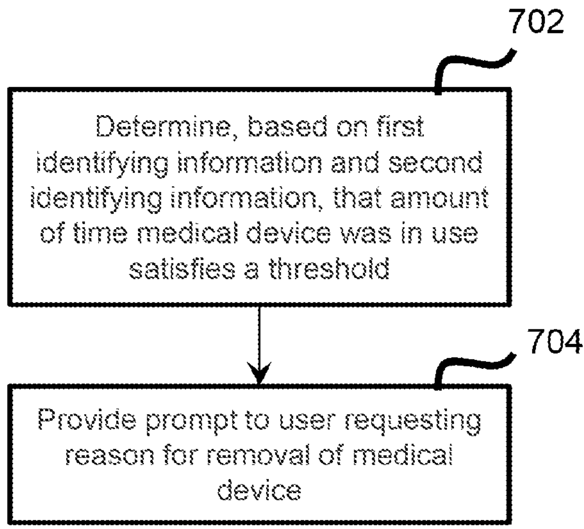

Referring now to FIG. 7, FIG. 7 is a flowchart of non-limiting embodiments or aspects of a process 700 for medical waste tracking. In some non-limiting embodiments or aspects, one or more of the steps of process 700 may be performed (e.g., completely, partially, etc.) by medical waste tracking device 102. In some non-limiting embodiments or aspects, one or more of the steps of process 700 may be performed (e.g., completely, partially, etc.) by another device or a group of devices separate from or including medical waste tracking device 102, such as computing system 108 (e.g., one or more devices of computing system 108).

As shown in FIG. 7, at step 702, process 700 includes determining, based on first identifying information and second identifying information, that an amount of time that a medical device was in use satisfies a threshold. For example, medical waste tracking device 102 may determine, based on the first identifying information (e.g., a first time stamp associated with the first identifying information, etc.) and the second identifying information (e.g., a second time stamp associated with the second identifying information, etc.), that an amount of time that medical device 104 was in use satisfies a threshold. As an example, medical waste tracking device 102 may determine that a final or total dwell time for medical device 104 is greater than a threshold associated with a failed catheter insertion or stick, but less than an allowed dwell time for medical device 104.

As shown in FIG. 7, at step 704, process 700 includes providing, in response to determining that an amount of time that a medical device was in use satisfies a threshold, a prompt to a user, the prompt including a request for the user to input a reason for removal of the medical device. For example, medical waste tracking device 102 may provide, in response to determining that the amount of time that medical device 104 was in use satisfies the threshold, a prompt to a user, the prompt including a request for the user to input a reason for removal of medical device. As an example, a user or clinician may enter a reason for removal of medical device 104 to medical waste tracking system 102 and/or computing system 108 (e.g., via input component 310 of medical waste tracking system 102, via input component 310 of computing system 108, etc.).

Figure 8:
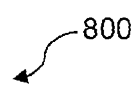
FIG. 8 is a flowchart of non-limiting embodiments or aspects of a process for medical waste tracking.
Figure 8:
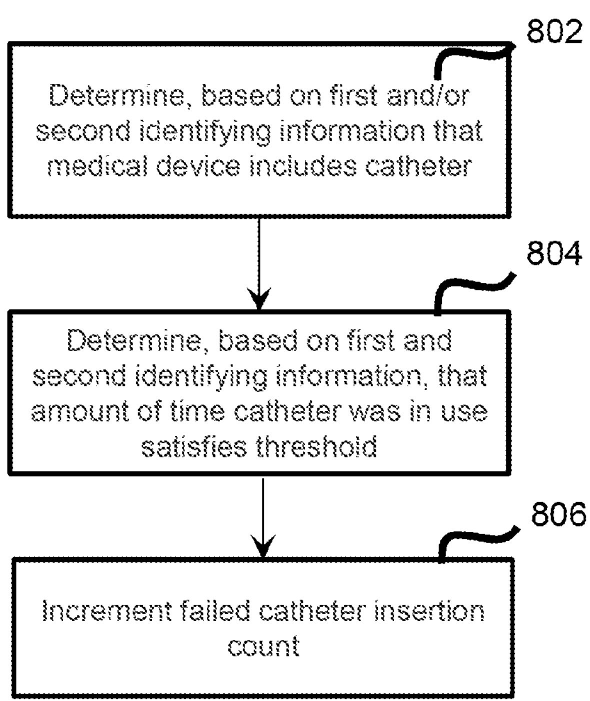

Referring now to FIG. 8, FIG. 8 is a flowchart of non-limiting embodiments or aspects of a process 800 for medical waste tracking. In some non-limiting embodiments or aspects, one or more of the steps of process 800 may be performed (e.g., completely, partially, etc.) by medical waste tracking device 102. In some non-limiting embodiments or aspects, one or more of the steps of process 800 may be performed (e.g., completely, partially, etc.) by another device or a group of devices separate from or including medical waste tracking device 102, such as computing system 108 (e.g., one or more devices of computing system 108).

As shown in FIG. 8, at step 802, process 800 includes determining, based on at least one of first identifying information and second identifying information, that a medical device includes a catheter. For example, medical waste tracking device 102 may determine, based on at least one of the first identifying information and the second identifying information, that medical device 104 includes a catheter.

As shown in FIG. 8, at step 804, process 800 includes determining, based on first identifying information and second identifying information, that an amount of time that the catheter was in use satisfies a threshold. For example, medical waste tracking device 102 may determine, based on the first identifying information and the second identifying information (e.g., based on first and second time stamps associated with the first and second identifying information, etc.), that an amount of time that the catheter was in use satisfies a threshold. As an example, medical waste tracking device 102 may determine whether an final or total dwell time of the catheter is less than a threshold time (e.g., 5 minutes, etc.) associated with a filed catheter insertion or stick attempt.

As shown in FIG. 8, at step 806, process 800 includes incrementing, in response to determining that an amount of time that a catheter was in use satisfies a threshold, a count associated with a number of catheter insertion attempts for an insertion site of a patient. For example, medical waste tracking device 102 may increment, in response to determining that the amount of time that the catheter was in use satisfies the threshold, a count associated with a number of catheter insertion attempts for an insertion site of the patient.

Although embodiments or aspects have been described in detail for the purpose of illustration and description, it is to be understood that such detail is solely for that purpose and that embodiments or aspects are not limited to the disclosed embodiments or aspects, but, on the contrary, are intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment or aspect. In fact, many of these features can be combined in ways not specifically recited in the claims and/or disclosed in the specification. Although each dependent claim listed below may directly depend on only one claim, the disclosure of possible implementations includes each dependent claim in combination with every other claim in the claim set.

What is claimed is:

1. A method comprising:

receiving, with an opening in a housing of a medical waste tracking device of a plurality of medical waste tracking devices on a same network, a package for a medical device, wherein the opening in the housing of the medical waste tracking device includes a base configured to move to connect the opening to an interior of a receptacle configured to hold medical waste including the package for the medical device and the medical device;

in response to the package for the medical device being received in the opening, automatically reading, with a sensor of the medical waste tracking device, first identifying information from a first information element encapsulating the first identifying information on the package for the medical device;

in response to the sensor of the medical waste tracking device reading the first identifying information from the first information element encapsulating the first identifying information on the package, controlling, with at least one processor, the base to move to connect the opening to the interior of the receptacle to deposit the package into the interior of the receptacle, wherein the first identifying information is associated with a first time including a time of deposit of the package into the interior of the receptacle and representing a start of use for the medical device for indwelling treatment of a patient;

generating, with at least one processor, based on the first identifying information and a current time, a dwell time indicating an amount of time that the medical device is used for treatment of the patient, wherein the dwell time is determined based on a difference between the first time including the time of deposit of the package into the interior of the receptacle and representing the start of use for the medical device for indwelling treatment of the patient and the current time;

before the medical device is received at one of the plurality of medical waste tracking devices, determining, with at least one processor that the dwell time satisfies a threshold dwell time associated with the medical device, wherein the threshold dwell time corresponds to a dwell-time limit for the medical device based on a time of package disposal to a time of medical device disposal or lack thereof;

providing, with at least one processor, in response to determining that the dwell time satisfies the threshold dwell time, an alert to a user, wherein the alert includes a recommendation to at least one of remove and replace the medical device that is in use for treatment of the patient;

in response to the medical device being received at the one of the plurality of medical waste tracking devices, automatically reading, with a corresponding sensor of the one of the plurality of medical waste tracking devices, second identifying information from a second information element encapsulating the second identifying information on the medical device;

in response to reading the second identifying information from the second information element encapsulating the second identifying information on the medical device, controlling, with at least one processor, a corresponding base of the one of the plurality of medical waste tracking devices to deposit the medical device into a corresponding receptacle of the one of the plurality of medical waste tracking devices, wherein each of the first identifying information and the second identifying information includes a same unique device code associated with the medical device, wherein the first identifying information further includes a first indicator indicating that the first identifying information is associated with the package for the medical device, wherein the second identifying information further includes a second indicator indicating that the second identifying information is associated with the medical device, and wherein the deposit of the package into the interior of the receptacle of the medical waste tracking device is linked to the deposit of the medical device at the one of the plurality of medical waste tracking devices with the same unique device code at different ones of the plurality of medical waste tracking devices on the same network; and providing, with at least one processor, based on the second identifying information, an indication that the medical device is not in use for treatment of the patient.

2. The method of claim 1, further comprising:

associating, with at least one processor, the medical waste tracking device with at least one of a room and the patient assigned to the room.

3. The method of claim 1, wherein the sensor of the medical waste tracking device reads the first identifying information from the first information element via a short range wireless communication protocol.

4. The method of claim 1, wherein the sensor of the medical waste tracking device includes at least one of the following: an optical sensor, an acoustic sensor, or any combination thereof, and wherein the sensor of the medical waste tracking device reads the first identifying information from the first information element with the at least one of the optical sensor and the acoustic sensor.

5. The method of claim 1, further comprising:

transmitting, with a wireless communication device of the medical waste tracking device, the first identifying information to a computing device.

6. The method of claim 5, further comprising:

establishing, with a corresponding wireless communication device of the one of the plurality of medical waste tracking devices, a communication connection with the medical device before the medical device is received at the one of the plurality of medical waste tracking devices;

forwarding, with the corresponding wireless communication device of the one of the plurality of medical waste tracking devices, when the medical device is in use, information received from the medical device to the computing device.

7. The method of claim 1, further comprising:

determining, with at least one processor, based on the first identifying information and the second identifying information, that an amount of time that the medical device was in use satisfies a threshold; and providing, with at least one processor, in response to determining that the amount of time that the medical device was in use satisfies the threshold, a prompt to the user, wherein the prompt includes a request for the user to input a reason for removal of the medical device.

8. The method of claim 1, further comprising:

determining, with at least one processor, based on at least one of the first identifying information and the second identifying information, that the medical device includes a catheter;

determining, with at least one processor, based on the first identifying information and the second identifying information, that an amount of time that the catheter was in use satisfies a threshold;

incrementing, with at least one processor, in response to determining that the amount of time that the catheter was in use satisfies the threshold, a count associated with a number of catheter insertion attempts for an insertion site of the patient.

9. The method of claim 1, further comprising:

determining, with a corresponding scale of the one of the plurality of medical waste tracking devices, a weight of a fluid received at the one of the plurality of medical waste tracking devices; and determining, with at least one processor, an amount of fluid loss associated with the patient based on the weight of the fluid.

10. The method of claim 1, further comprising:

determining, with at least one processor, based on the second identifying information, a type of the medical device; and providing, with the at least one processor, based on the type of the medical device, a prompt to the user, wherein the prompt includes a request for the user to dispose of the medical device with a different medical waste tracking device of the plurality of medical waste tracking devices.

11. The method of claim 1, wherein the corresponding base of the one of the plurality of medical waste tracking devices is configured to move to connect the corresponding opening of the one of the plurality of medical waste tracking devices to a first subdivision of the interior of the corresponding receptacle or a second subdivision of the interior of the corresponding receptacle, and wherein the method further comprises:

determining, with the at least one processor, based on the second identifying information, a type of the medical device; and controlling, with the at least one processor, the corresponding base to move to connect the corresponding opening to the interior of the corresponding receptacle that includes the first subdivision of the corresponding receptacle or the second subdivision of the corresponding receptacle, based on the type of the medical device, to deposit the medical device into one of the first subdivision of the corresponding receptacle or the second subdivision of the corresponding receptacle.

12. The method of claim 1, further comprising:

disabling, with the one of the plurality of medical waste tracking devices, a communications capability of the medical device received at the one of the plurality of medical waste tracking devices.

13. The method of claim 1, further comprising:

establishing, with a wireless communication device of the medical waste tracking device and a corresponding wireless communication device of the one of the plurality of medical waste tracking devices, at least one of the following: (i) a communication connection between the wireless communication device and the corresponding wireless communication device, (ii) a communication connection between the wireless communication device and a computing device and a communication connection between the corresponding wireless communication device and the computing device, or any combination thereof.

14. The method of claim 1, wherein at least one of the medical waste tracking device or the one of the plurality of medical waste tracking devices includes the at least one processor.

15. The method of claim 1, wherein the at least one processor is included in a computing device external to the medical waste tracking device and the one of the plurality of medical waste tracking devices.

* * * * *